United States Patent [19]

Curran et al.

[11] 4,000,142
[45] Dec. 28, 1976

[54] PROCESS FOR PREPARING PYRIDINE DERIVATIVES

[75] Inventors: Adrian Charles Ward Curran, Newcastle-upon-Tyne; Robin Gerald Shepherd, Maidenhead, both of England

[73] Assignee: John Wyeth & Brother Limited, Maidenhead, England

[22] Filed: Nov. 25, 1974

[21] Appl. No.: 526,565

[30] Foreign Application Priority Data

Dec. 17, 1973 United Kingdom ............ 58307/73
Feb. 4, 1974 United Kingdom ............ 4956/74
Mar. 27, 1974 United Kingdom ............ 13514/74
July 12, 1974 United Kingdom ............ 30934/74

[52] U.S. Cl. .................. 260/287 T; 260/283 R; 260/283 SC; 260/283 CN; 260/283 S; 260/286 R; 260/287 F; 260/290 HL; 260/290 R; 260/290 S; 260/294.8 C; 260/294.9; 260/295 K; 260/448.2 E; 260/448.2 N

[51] Int. Cl.$^2$ ............ C07D 215/48; C07D 215/14
[58] Field of Search ..... 260/283 CN, 287 T, 283 S, 260/287 F, 283 SC, 448.2 E, 448.2 N, 294.8 C, 294.9, 295 K, 286 R

[56] References Cited

FOREIGN PATENTS OR APPLICATIONS 2,352,585   5/1974   Germany ............ 260/287 T

*Primary Examiner*—Donald G. Daus
*Assistant Examiner*—Mary C. Vaughn

[57] ABSTRACT

The invention relates to a process for preparing pyridine compounds which have a fused cycloalkane ring containing an amide, thioamide or nitrile group. The process involves treating a metal derivative of the pyridine compound with a silyl isocyanate or isothiocyanate and then subjecting the product to hydrolysis or alcoholysis.

10 Claims, No Drawings

PROCESS FOR PREPARING PYRIDINE DERIVATIVES

The invention relates to a new process for preparing pyridine derivatives.

The invention provides a process for preparing compounds of formula I

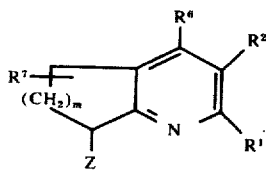
(I)

and acid addition salts thereof, wherein Z is $CONH_2$, $CSNH_2$ or CN, $R^1$, $R^2$ and $R^6$ are the same or different and represent hydrogen, trifluoromethyl, or an alkyl, aralkyl or aryl radical, any of which radicals may be substituted by alkyl, nitro or trifluoromethyl or $R^1$ and $R^2$ taken together represent an alkylene chain —$CH_2(CH_2)_nCH_2$— wherein $n$ is 1, 2 or 3, $R^7$ represents single or multiple substitution by hydrogen, or alkyl, aralkyl or aryl radicals any of which radicals may be substituted by alkyl, nitro or trifluoromethyl and when $R^1$ and $R^2$ taken together form an alkylene chain the resulting ring may be substituted by one or more $R^7$ radicals as defined above, and $m$ is 1, 2 or 3, which process comprises treating a compound of formula II

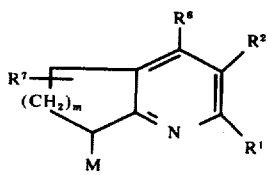
(II)

wherein $R^1$, $R^2$, $R^6$, $R^7$ and $m$ are as defined in connection with formula I above and M is sodium, potassium, lithium or MgHal where Hal is chlorine, bromine or iodine, with a silyl compound of formula $R_xSi(NCY)_{4-x}$ wherein R is an alkyl, aryl or aralkyl residue and $R_x$ may be any mixture of these, Y is oxygen or sulphur and $x$ has a value from 0 to 3 then subjecting the product to hydrolysis or alcoholysis, with the proviso that when a compound of formula I in which Z is CN is desired the molar ratio of compound $R_xSi(NCY)_{4-x}$ to compound IIa is at least 2:1 and $x$ is 3 and Y is S.

Compounds of formula I in which Z is $CSNH_2$ or CN display pharmacological activity, namely anti-ulcer and/or antisecretory activity. [Compounds where Z is $CONH_2$ are intermediates.]

Examples of the compound $R_xSi(NCY)_{4-x}$ are:

$x = 0:Si(NCH)_4$ $x = 1:RSi(NCY)_3$ $x = 2:R_2Si(NCY)_2$ $x = 3:R_3SiNCY$ wherein R has any of the meanings given above.

When $x$ is 3 the residue $R_xSi$ may be a tri-alkyl-, tri-aryl- or tri-aralkyl-silyl group and is preferably a tri-lower alkyl silyl group, e.g. trimethylsilyl.

The reaction with the compound of formula $R_xSi(NCY)_{4-x}$ is conducted under anhydrous conditions, preferably in an inert solvent, for example a hydrocarbon solvent such as benzene, toluene or hexane. Ethers including cyclic ethers such as tetrahydrofuran should be avoided. Conveniently the starting material of formula II is prepared in situ and the same solvent is used for the reaction with the compound of formula $R_xSi(NCY)_{4-x}$. However, where a compound of formula II wherein Z is MgHal is used these are usually prepared in ether as solvent. The ether is removed and the reaction with the silicon compound is conducted in a different solvent.

The product of the first stage is a compound of formula III

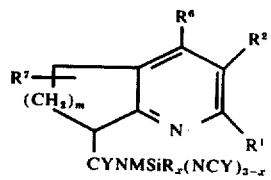
(III)

(wherein $R^1$, $R^2$, $R^6$, $R^7$ and $m$ are as defined in connection with formula I and Y, M, R and x are as defined above) which is converted by water or alcohol to the desired compound of formula I, presumably via a transient intermediate of formula IV

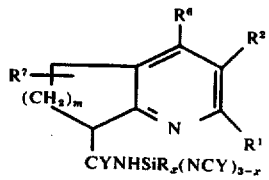
(IV)

wherein R is the organic residue above and Y is oxygen or sulphur and M, $R^1$, $R^2$, $R^6$, $R^7$, $m$ and $x$ are as defined in connection with formula II above.

Compounds of formula III and IV are included in the present invention as is the process for preparing them described above. These compounds are not isolated but are obtained and used in solution.

The desired compound of formula I wherein Z is $CONH_2$, or $CSNH_2$ is conveniently formed by treating a compound of formula III with water or a lower alcohol, e.g. ethanol.

The starting materials of formula II wherein M is sodium potassium or lithium are described in German Offenlegungsschrift 2,352,585 or may be prepared by analogous methods. They may be prepared by reacting a compound of formula I wherein Z is hydrogen with a metal alkyl e.g. $MR^{10}$ wherein M is sodium, potassium or lithium and $R^{10}$ is alkyl, aryl or aralkyl.

It has been found that when a compound of formula I in which $R^1$ is methyl and $R^2$, $R^6$ and $R^7$ are hydrogen and M is hydrogen is treated with metal alkyl the metal atom may be inserted either at the desired position or in the methyl group $R^1$. This side reaction may also occur with any compound containing an alkyl group $R^1$ in which there are one or two hydrogen atoms on the carbon atom adjacent to the pyridine ring. These by-products which contain a metal atom in an alkyl group $R^1$ do not normally react with alkyl-silyl isothiocyanates.

Compounds of formula II where M is MgHal may be prepared by treating a compound of formula I wherein Z is hydrogen with an alkyl magnesium halide $R^{11}MgHal$ wherein $R^{11}$ is an alkyl group, preferably a lower akyl group, and Hal is chlorine, bromine or iodine. $R^{11}$ may be a straight or branched chain alkyl group, the isopropyl group being preferred. Conveniently the compound of formula II is prepared in situ. If ether is used as a solvent this is distilled off and another solvent added after which the product is then treated with the compound of formula $R_xSi(NCY)_{4-x}$, followed by hydrolysis or alcoholysis to obtain the desired compound of formula I.

When any of $R^1$, $R^2$, $R^6$ or $R^7$ is an alkyl radical it is preferred that this is a lower alkyl radical which may be a straight or branched chain, having from 1 to 6 carbon atoms, e.g. methyl, ethyl, n-, and iso-propyl and n-, s- and t-butyl, $R^7$ may be a gem-dimethyl group and when a single radical may be on the same carbon atom as the group Z. The term alkyl radical is also intended to embrace cyclic alkyl radicals e.g. cyclobutyl, cylopentyl and cyclohexyl. When any of $R^1$, $R^2$, $R^6$ or $R^7$ is an aralkyl radical it is preferred that this is an aryl-lower alkyl radical where the lower alkyl portion may be as discussed above for a lower alkyl radical. The aryl portion is preferably a phenyl radical.

When any of $R^1$, $R^2$, $R^6$ or $R^7$ is an aryl radical, this is preferably phenyl or a substituted phenyl radical (substituted by alkyl, nitro or trifluoromethyl). However, other aryl radicals which may be used include naphthyl.

Particularly preferred compounds are bicyclic compounds especially those in which one of $R^1$, $R^2$ and $R^6$ is ethyl, the others are hydrogen and $R^7$ is hydrogen. Tricyclic compounds may be symmetrical (.i.e. $n$ and $m$ are equal) or unsymmetrical i.e. $n$ and $m$ are different.

Also preferred are compounds where $m$ is 2.

We have found that by conducting the above reaction with a compound (II) and a compound of formula $R_3SiNCS$ wherein the molar ratio exceeds 2:1 a compound of formula I wherein Z is cyano is obtained in addition to the compound of formula I wherein Z is $CSNH_2$.

For the preparation of compounds where Z is $CSNH_2$ or or $CONH_2$ it is preferred that the ratio of the silyl compound to the compound of formula II is in the range 0.5:1 to 2:1, eg 0.5:1 to 1.5.

With higher ratios e.g. 4:1 the cyano compound has been obtained exclusively in certain instances.

Accordingly the present invention provides in one aspect a process for preparing a compound of formula I as defined above wherein Z is cyano which comprises treating a comound of formula (II) as defined above with a compound of formula $R_3SiNCS$ in at least 2:1 molar ratio, wherein R is an alkyl, aryl or aralkyl residue or $R_x$ is any mixture of these and subjecting the product to hydrolysis or alcoholysis.

We have also found that yields of the final product of formula I wherein Z is $CONH_2$ or $CSNH_2$ may be improved if the reaction with the metal alkyl is conducted in the presence of a secondary amine (preferably in a molar amount equal to that of the metal alkyl) and then followed by reaction with the silyl isothiocyanate or isocyanate. This may be achieved conveniently by preparing the starting material of formula II wherein M is lithium sodium or potassium in situ by reaction of a compound of formula II wherein M is hydrogen with a metal amide derived from a secondary amine.

Accordingly the present invention provides in another aspect a process for preparing a compound of formula I, as defined above, in which a corresponding compound of formula I wherein Z is hydrogen is treated with a metal amide MA wherein M is sodium, potassium or lithium and A is a secondary amine radical, and then treating the product with a compound of formula $R_xSi(NCY)_{4-x}$ as defined above and then subjecting the product to hydrolysis or alcoholysis.

The metal amide may be formed in situ by reacting a metal $MR^{10}$ wherein M is sodium, potassium or lithium and $R^{10}$ is alkyl, aryl or aralkyl with a secondary amine, (preferably in a molar amount equal to that of the metal alkyl). The compound of formula I wherein X is hydrogen may then be added.

Preferably the metal M is lithium. The secondary amine may be a dialkylamine e.g. diethylamine, di-isopropylamine, di-tertiarybutyl amine, di-n-decylamine, dicyclohexylamine, N-tertiaryamyl-N-t-butylamine, N-isopropyl-N-cyclohexylamine, or N(1'-ethylcyclohexyl)-1,1,3,3,tetramethylbutylamine, or a cyclic compound e.g. piperidine, or 2,2,6,6-tetramethylpiperidine.

The following examples illustrate the invention. Temperatures are in °C.

EXAMPLE 1

3-Methyl-5,6,7,8-tetrahydroquinoline-8-thiocarboxamide

A solution of 3-methyl-5,6,7,8-tetrahydroquinoline (7.3 g., 0.05 mol.) in hexane (50 ml.) was cooled to 0° C and treated dropwise with stirring with a 15% w/w solution of butyl lithium in hexane (26 ml., 0.06 mol.) in an atmosphere of nitrogen. The reaction mixture was stirred at 0° C for an additional 1 hour and was added portionwise to a slution of trimethylsilylisothiocyanate (13.1 g., 0.1 mol.) in hexane (50 ml.) and under nitrogen keeping the internal temperature at −20° C. The reaction mixture was stirred for an additional 30 minutes at −20° C, allowed to warm to room temperature and diluted with water (50 ml.). The pH was adjusted to 2.0 with conc. HCl and the hexane layer separated and discarded. The aqueous solution was adjusted to pH 10.0 with sodium carbonate and extracted with ethyl acetate (3 × 50 ml.). The combined extracts were dried ($MgSO_4$) and the solvent removed in vacuo. The residue was trituratd with n-hexane and solid filtered and recrystallised from benzene to give the title compound as colourless needles (3.5 g., 39%) m.p. 153° identical in all respects to authentic material. (Found: C, 64.6; H, 7.0; N, 13.9%. $C_{11}H_{14}N_2S$ Requires: C, 64.1; H, 6.8; N, 13.6%). The hexane soluble material was distilled to give recovered 3-methyl-5,6,7,8-tetrahydroquinoline (3.5 g., 50%) b.p. 120°/15 mm.

EXAMPLE 2

3-Methyl-5,6,7,8-tetrahydroquinoline-8-carboxamide

A solution of 3-methyl-5,6,7,8-tetrahydroquinoline (7.3 ., 0.05 mol.) in hexane (50 ml.) was cooled to 0° C and treated dropwise with 15w/w butyllithium in hexane (26 ml., 0.06 mol.) in a nitrogen atmosphere. The reaction mixture was allowed to stand at 0° C for 1 hour and was then added dropwise over 30 minutes to a solution of trimethylsilylisocyanate (19.5 g., 0.17 mol.) in hexane (50 ml.) keeping the internal temperature at −20° C. The reaction mixture was allowed to stand at −20° C for 1 hour and was then diluted with water (50 ml.) and the pH adjusted to 2.0 with conc. HCl. The hexane layer was separated and discarded and the aqueous solution adjusted to pH 10.0 wih sodium carbonate and extracted with chloroform (3 × 25 ml.). The combined extracts were washed with saturated brine, dried and the solvent removed in vacuo. The residue was triturated with n-hexane, filtered and the solid crystallised from ethyl acetate to give the title compound as colourless needles (3.1 g., 35%) m.p. 104° C. identical in all respects to the authentic material (when crystallised from ethyl acetate). Analysis: Found C, 69.1; 7.4; N, 14.7. $C_{11}H_{14}N_2O$ requires C, 69.5; H, 7.4; N, 14.7. The hexane soluble material was distilled to give recovered 3-methyl-5,6,7,8-tetrahydroquinoline (4.2 g.) b.p. 120°/15mm.

EXAMPLE 3

8-Cyano-3-methyl-5,6,7,8-tetrahydroquinoline

A solution of 3-methyl-5,6,7,8-tetrahydroquinoline (29 g., 0.2 mol) in benzene (200 ml.) was cooled to 0° C and treated dropwise with a 15% w/w solution of n-butyl lithium in hexane (88 ml., 0.2 mol) under nitrogen. After 1 hour at 0° C the reaction mixture was added portionwise to a solution of trimethylsilylisothiocyanate (112 ml., 0.8 mol.) in benzene (200 ml.) at 0° C and under nitrogen. After 2½ hours at room temperature the reaction mixture was treated with water (100 ml.) and with 2N HCl to pH 2.0. The aqueous layer was separated, washed with ethyl acetate (1 × 50 ml.) and the pH adjusted to 9.0 with sodium carbonate and extracted with chloroform (3 × 100 ml.) The combined chloroform extracts were dried ($MgSO_4$) and the solvent removed in vacuo to give a red oil which was distilled first at 0.25 mmHg to give recovered 3-methyl-5,6,7,8-tetrahydroquinoline (17 g., 59%) b.p. 54–7° and then at 0.05 mmHg to give the title compound as a pale red oil (12 g. 35%) b.p. 115–20° $R_T = 4.1/4$ min. (3% SE30, 200° C) identical to authentic material.

EXAMPLE 4

4-Methyl-5,6,7,8-tetrahydroquinoline-8-thiocarboxamide

A solution of 4-methyl-5,6,7,8-tetrahydroquinoline (5.83 g., 0.04 mole) in dry benzene (40 ml.) was cooled to 0° and to the stirred solution was added dropwise a 15% w/w solution of butyl lithium in hexane (17.5 ml., 0.04 mole) under an atmosphere of nitrogen. The red reaction mixture was stirred at 0° for a further 30 minutes. Trimethylsilylisothiocyanate (5.6 ml., 0.04 mole) was then added dropwise, maintaining the temperature at 0°. After an additional 30 minutes, the mixture was allowed to warm to room temperature and diluted with water (40 ml.) The pH was adjusted to 2.0 by addition of conc. HCl and the benzene layer separated and discarded. The aqueous phase was adjusted to pH 10.0 by adding anhydrous $Na_2CO_3$ and extracted with $CHCl_3$ (3 × 40 ml.). The $CHCl_3$ solution was then dried ($MgSO_4$), filtered and evaporated (reduced pressure) to afford an oil (5.77 g.). Addition of ether caused crystallisation of the title compound as colourless needles. Filtration afforded 0.69 g. of base which was converted to the hydrochloride by dissolving in a minimum of EtOH, adding EtOH/HCl until just acid followed by ether to induce crystallisation. Filtration provided the title compound hydrochloride as colourless needles, (0.64 g.), m.p. 213° C. Analysis: Found: C, 54.95; H, 6.40; N, 11.52 $C_{11}H_{14}N_2S.HCl$ requires C, 54.42; H, 6.23; N, 11.54%

EXAMPLE 5

3,7,7-Trimethyl-5,6,7,8-tetrahydroquinoline-8-thiocarboxamide hydrochloride

A solution of 3,7,7,-trimethyl-5,6,7,8-tetrahydroquinoline (10.3 g. 59 m. mole) in hexane (50 ml.) was cooled to 0° C and treated dropwise with a 15% w/w solution of butyl lithium in hexane (25.8 ml., 59 m. mole) and allowed to stand at 0° for 1 hour. The solution was treated dropwise with trimethylsilylisothiocyanate (8.25 ml., 59 m. mole) in hexane (50 ml.) and allowed to stand at 0° C for 1½ hour. The reaction mixture was warmed to room temperature diluted with water (25 ml.) and the pH adjusted to 1.0 with conc. HCl. The solution was extracted with ether (3 × 25 ml.) and the aqueous phase adjusted to pH 10.0 with sodium carbonate and extracted with chloroform (3 × 50 ml.). The combined extracts were washed with brine, dried ($MgSO_4$) and the solvent removed. The residual oil (12.6 g.) was chromatographed on silica gel and eluted with methanol-chloroform. Recovered 3,7,7-trimethyl-5,6,7,8-tetrahydroquinoline (7.6 g.) was obtained by elution with 2% methanol-chloroform. Elution with 5% methanol-chloroform gave 3,7,7-trimethyl-5,6,7,8-tetrahydroquinoline-8-thiocarboxamide (2 g., 15%) as a yellow solid which was recrystallised from benzene-hexane as pale yellow needles and converted to the hydrochloride by dissolving in ether and treating with an excess of dry HCl. The resultant solid was recrystallised from isopropyl alcohol to give the one and a quarter hydrate of the title compound as colourless needles m.p. 162° C. (Found C, 53.3; H, 7.35; N, 9.5. $C_{13}H_{18}N_2S.HCl.1.1/4H_2O$ requires: C, 53.3; H, 7.4; N, 9.55%).

EXAMPLE 6

3-Methyl-5,6,7,8-tetrahydroquinoline-8-thiocarboxamide

Following the general procedure of Example 1 but using different molar ratios of trimethylsilylisothiocyanate (TMS.NCS): 8-Lithio-3-methyl-5,6,7,8-tetrahydroquinoline (LiTHQ) (prepared from equimolar aounts of butyl lithium and 3-methyl-5,6,7,8-tetrahydroquinoline) the following results were obtained.

| Molar Ratio* TMSNCS:LiTHQ | Yield** i.e. % THQ converted to title product | Yield as % TMS-NCS converted to title product |
|---|---|---|
| 0.5:1 | 35 | 70 |
| 0.8:1 | 34 | 42 |
| 1:1 | 30–40 | 30–40 |
| 1.2:1 | 36 | 30 |
| 1.5:1 | 39 | 26 |
| 2:1 | 30*** | 15*** |

\* solvent benzene
\*\* quantitative recovery of unconverted 3-methyl-5,6,7,8-tetrahydroquinoline(THQ)
\*\*\*8-nitrile (10%) also obtained

EXAMPLE 7

3-Methyl-5,6,7,8-tetrahydroquinoline-8-thiocarboxamide

3-Methyl-5,6,7,8-tetrahydroquinoline (7.3g, 0.05 mol.) was added to a solution of isopropylmagnesium bromide [prepared from isopropylbromide (6.15g, 0.05 mol), magnesium (1.44g, 0.06 mol) in ether (10 ml.)] and the solution heated at 60° to remove the ether by distillation. Toluene (5 ml.) was added and the reaction mixture was heated at 120° for 2 hours, cooled, diluted with toluene (30 ml) and this solution was added to a solution of trimethylsilyl isothiocyanate (7.85 g, 0.06 mol) in toluene (50 ml.) at 0° C. The reaction mixture was stirred at room temperature for 12 hours, diluted with water (15 ml.) and the pH adjusted to 2.0 with Conc. HCl. The aqueous solution was extracted with ether and the extracts discarded. The aqueous solution was adjusted to pH 9.0 with $Na_2CO_3$ and extracted with chloroform (3 × 50 ml.). The combined extracts were washed with brine, dried and the solvent removed to give a mixture of 3-methyl-5,6,7,8-tetrahydroquinoline and the title compound (5%) which was isolated by chromatography and identified by comparison with authentic material.

EXAMPLE 8

2,3,5,6,7,8-Hexahydro-1H-cyclopenta[b]-quinoline-5-thiocarboxamide 2-(2'-Oxocyclopentyl)methyl cyclohexanone was prepared from 2-(dimethylaminomethyl)cyclohexanone and cyclopentanone according to the method described in Ann. Chim. 1963, 53 (6), 819 and was isolated as a colourless oil in 80% yield b.p. 92°/0.05 mm.

2,3,5,6,7,8-hexahydro-1H-cyclopenta[b]-quinoline was prepared from 2-(2'-oxocyclopentyl)methyl cyclohexanone according to the method described in Ann. Chim., 1963, 53 (6), 819 and was isolated in 65% yield as a colourless oil b.p. 80°/0.05 mm.

The hydrochloride was prepared for characterisation by treating an ethereal solution of the base with ethereal HCl and was isolated as the hemihydrate as colourless needles from ethanol-ether. m.p. 104° C.

(Found: C, 65.7, H, 7.8; N, 6.6. $C_{12}H_{16}N.HCl. \frac{1}{2}H_2O$ requires: C, 65.8; H, 7.8; N, 6.4%.)

A solution of 2,3,5,6,7,8-hexahydro-1H-cyclopenta[b]quinoline (5.19g., 0.03mol) in benzene (5 ml.) was cooled to 0° C and treated with a 15% w/w solution of butyl lithium in hexane (13.5ml., 0.03 mol.) and allowed to stand at 0° C for 1 hour.

The reaction mixture was treated dropwise with a solution of trimethylsilylisothiocyanate (4.5ml, 0.03mol) in benzene (2 ml.) with cooling in ice. The reaction mixture was stirred at 0° C for an additional 1 hour, diluted with water (15 ml.) and the pH adjusted to 2.0 with 2N HCl. The solution was extracted with ethyl acetate (3 × 50 ml.) and the extracts discarded. The aqueous solution was adjusted to pH 9.0 with $Na_2CO_3$ and extracted with chloroform (3 × 50 ml.).

The combined extracts were washed with brine, dried ($MgSO_4$) and the solvent removed in vacuo.

The residual oil was diluted with n-hexane (100ml.) and cooled to 0° C. The precipitated solid was filtered, recrystallised from isopropanol, dissolved in ether and treated with excess ethereal HCl. The resultant solid was recrystallised from ethanol-ether to give the hydrochloride monohydrate of the title compound (0.9g) m.p. 118° C (Found: C, 54.6; H, 6.3; N, 10.0. $C_{13}H_{16}N_2S.HCl.H_2O$ requires: C, 54.4; H, 6.6; N, 9.8%).

EXAMPLE 9

3-Methyl-5,6,7,8-tetrahydroquinoline-8-thiocarboxamide

A solution of di-isopropylamine (11.11 g., 0.11 mol) in benzene (50 ml.) was cooled to 0° C and treated portionwise with a 9% w/v solution of butyl lithium in hexane (79 ml., 0.11 mol.). After 45 minutes at 0° C the solution was treated dropwise with 3-methyl-5,6,7,8-tetrahydroquinoline (14.7 g., 0.10 mol.) with rapid stirring and under an atmosphere of nitrogen. After 1½ hours at 0° C the red suspension was treated portionwise over 2 minutes with trimethylsilylisothiocyanate (14.7 ml., 0.11 mol.) and the reaction mixture stirred at 0° C for ½ hour and at room temperature for 1 hour. The reaction mixture was diluted with water (25 ml.) and the pH adjusted to 2.0 with 2N HCl. The mixture was extracted with ethylacetate (3 × 25 ml.) and the combined extracts discarded. The aqueous solution was adjusted to pH 10.0 with sodium carbonate and extracted with chloroform (3 × 50 ml.). The combined extracts were washed with saturated brine (1 × 50 ml.), dried ($MgSO_4$) and the solvent removed in vacuo. The residual oily solid was triturated with n-hexane (100 ml.) and the solid filtered and recrystallised from isopropanol to give the title compound as pale yellow needles (8.9 g., 43%) m.p. 153° C identical in all respects to authentic material. The filtrate was analysed by g.l.c. (10% SE30, T = 160° C and identified as a mixture of 8-cyano-3-methyl-5,6,7,8-tetrahydroquinoline (1 g., 6% yield based on starting material) and recovered 3-methyl-5,6,7,8-tetrahydroquinoline (7.17 g., 48% yield based on starting material).

EXAMPLE 10

5,6,7,8-Tetrahydroquinoline-8-thiocarboxamide

A solution of di-isopropylamine (33.3g, 0.33 mol) in benzene (150 ml) was cooled in ice and treated with 9% w/v butyl-lithium in hexane (237 ml, 0.33 mol). After 45 minutes the solution was treated with 5,6,7,8-tetrahydroquinoline (39.9 g, 0.3 mol) dropwise with stirring. After 1.5 hours trimethylsilyl-isothiocyanate (43.2 ml. 0.3 mol) was added and the resulting solution was allowed to stand at 0° C for 0.5 hours and at room temperature for 1 hour. Water (50 ml.) was added and the resulting mixture acidified with 2N HCl. The acid solution was separated, washed with ethyl acetate and the pH was adjusted to 9 with solid sodium carbonate. Extraction with chloroform followed by drying of the extract over $MgSO_4$, filtration and evaporation gave a thick gum which crystallised on trituration with n-hexane. Recrystallisation from methanol gave 5,6,7,8-tetrahydroquinoline-8-thiocarboxamide (16g, 30%) m.p. 160°. The hydrochloride was prepared by dissolution of the free base in hot iso-propyl alcohol adding ethereal HCl solution and allowing to crystallise. m.p. 263–4°.

(Found: C, 52.6; H, 6.0; N, 12.2. $C_{10}H_{12}N_2S$, HCl requires C, 52.5; H, 5.7; N, 12.3%).

EXAMPLE 11

4-Methyl-5,6,7,8-tetrahydroquinoline-8-thiocarboxamide hydrochloride

A stirred solution of di-isopropylamine (12.2 ml, 0.085 mol) in benzene (100 ml) at 0° C was treated dropwise with a 9% w/v solution of butyl lithium in hexane (62 ml, 0.085 mol). After 1 hour at 0° C, 4- methyl-5,6,7,8-tetrahydroquinoline (12.8 g, 0.085 mol) was added dropwise and then after a further hour the anion was treated dropwise with trimethylsilyl isothiocyanate (12.2 ml, 0.095 mol). After 0.5 hours at 0° C and 0.5 hours at room temperature the reaction mixture was diluted with water (50 ml) and the pH adjusted to 2.0 with conc. HCl. The aqueous layer was separated and adjusted to pH 10.0 with solid sodium carbonate and extracted with chloroform (3 × 50 ml) and the combined extracts were dried over MgSO₄, filtered and the solvent was removed in vacuo. The residual oil was triturated with n-hexane to give 4-methyl-5,6,7,8-tetrahydroquinoline-8-thiocarboxamide (3.4g, 19%). The hydrochloride was prepared by dissolving in hot iso-propyl alcohol adding excess ethereal HCl solution and allowing to crystallise to give 4-methyl-5,6,7,8-tetrahydroquinoline-8-thiocarboxamide, hydrochloride m.p. 212–3° C. (Found: C, 54.9; H, 6.4; N, 11.5. $C_{11}H_{14}N_2S$. HCl requires C, 54.4; H, 6.2; N, 11.5%).

EXAMPLE 12

2-Ethyl-5,6,7,8-tetrahydroquinoline-8-thiocarboxamide

By the method described in Example 11 using di-isopropylamine (2 ml 0.014 mol) in benzene (20 ml), n-butyl lithium solution (9% w/v, 10 ml, 0.014 mol), 2-ethyl-5,6,7,8-tetrahydroquinoline (2.3 g, 0.014 mol) and trimethylsilyl isothiocyanate (2 ml 0.015 mol) was obtained 2-ethyl-5,6,7,8-tetrahydroquinoline-8-thiocarboxamide (600 mg, 20%) m.p. 73–5° C (Found: C, 65.25; H, 7.6; N, 12.75. $C_{12}H_{16}N_2S$ requires C, 65.4; H, 7.3; N, 12.7%).

EXAMPLE 13

2-Butyl-5,6,7,8-tetrahydroquinoline-8-thiocarboxamide

By the method described in Example 11 using di-isopropylamine (4.45 ml 0.03 mol) in benzene (50 ml), n-butyl lithium solution (9% w/v, 13.5 g, 0.03 mol), 2-butyl-5,6,7,8-tetrahydroquinoline (6 g, 0.03 mol) and trimethylsilyl isothiocyanate (4.45 ml 0.033 mol) was obtained 2-butyl-5,6,7,8-tetrahydroquinoline-8-thiocarboxamide (1.2g, 15%) m.p. 54–6° C. (Found: C, 68.0; H, 8.4; N, 11.2. $C_{14}H_{20}N_2S$ requires C, 67.8; H, 8.1; N, 11.3%).

EXAMPLE 14

2-Methyl-4-phenyl-5,6,7,8-tetrahydroquinoline-8-thiocarboxamide

By the method described in Example 11 using di-isopropylamine (11.2 ml 0.077 mol) in benzene (150 ml), n-butyl lithium solution (9% w/v, 57 ml, 0.077 mol), 2-methyl-4-phenyl-5,6,7,8-tetrahydroquinoline (17.7 g, 0.077 mol), and trimethylsilyl isothiocyanate (11.2 ml 0.087 mol) was obtained 2-methyl-4-phenyl-5,6,7,8-tetrahydroquinoline-8-thiocarboxamide (1.2 g, 5%) m.p. 174–5° C. (Found: C, 72.0; H, 6.7; N, 9.4. $C_{17}H_{18}N_2S$ requires C, 72.3; H, 6.4; N, 9.9%).

EXAMPLE 15

3,4-Dimethyl-5,6,7,8-tetrahydroquinoline-8-thiocarboxamide

By the method described in Example 11 using di-isopropylamine (4.9 ml 0.034 mol) in benzene (50 ml), n-butyl lithium solution (9% w/v, 25 ml, 0.034 mol), 3,4-dimethyl-5,6,7,8-tetrahydroquinoline (5.65ag, 0.034 mol) and trimethylsilyl isothiocyanate (4.9 ml, 0.038 mol) was obtained 3,4-dimethyl-5,6,7,8-tetrahydroquinoline-8-thiocarboxamide (0.4 g, 5%) m.p. 163–5° C.
(Found: C, 65.1; H, 7.8; N, 12.2. $C_{12}H_{16}N_2S$ requires C, 65.4; H, 7.3; N, 12.2%).

EXAMPLE 16

3-Methyl-5,6,7,8-tetrahydroquinoline-8-thiocarboxamide

To a solution of di-isopropylamine (4.44 g, 0.044 mole) in benzene (30 ml) at 0° C under nitrogen was added with stirring a solution of n-butyl-lithium in hexane (9% w/v, 31.6 ml, 0.044 mole) and the resulting solution was stirred for 1 h at 0° C. 3-Methyl-5,6,7,8-tetrahydroquinoline (5.86 g, 0.04 mole) was added and stirred for a further 1½ h. The reaction mixture was treated with dimethylsilyl di-isothiocyanate (7.66 g, 0.044 mole) and the mixture was stirred for 0.5 h at 0° C and at room temperature for 1 h. Water (50 ml) was added and the pH was adjusted to 2 with conc. HCl. The aqueous layer was separated, washed with ethyl acetate, and the pH was adjusted to 10 with solid sodium carbonate. The resulting mixture was extracted with ethyl acetate (3 × 50 ml). The combined extracts were dried (MgSO₄), filtered, and the solvent was removed in vacuo. The residue was triturated with n-hexane to give 3-methyl-5,6,7,8-tetrahydroquinoline-8-thiocarboxamide (0.9 g, 15%).

EXAMPLE 17

3-Methyl-5,6,7,8-tetrahydroquinoline-8-thiocarboxamide

A solution of 3-methyl-5,6,7,8-tetrahydroquinoline (1.43 g, 0.01 mole) in benzene (20 ml) was treated with n-butyl-lithium (15% w/w, 4.5 ml, 0.01 mole) and the solution was allowed to stand at room temperature for 0.5 h. The solution was then treated with a suspension of silicon tetraisothiocyanate (1.3 g, 0.005 mole) in benzene (5 ml) at 0° C. After 10 min., water (50 ml) was added and the mixture was stirred for 0.5 h at room temperature and then acidified with conc. HCl. The aqueous layer was separated, washed with ethyl acetate and the pH was adjusted to 10 with solid $Na_2CO_3$. The basic mixture was extracted with ethyl acetate (3 × 50 ml) and the combined organic extracts were dried (MgSO₄), filtered and evaporated. The residue was triturated with n-hexane to give 3-methyl-5,6,7,8-tetrahydroquinoline-8-thiocarboxamide (0.2 g, 10%).

We claim:
1. A process for preparing a compound of formula I

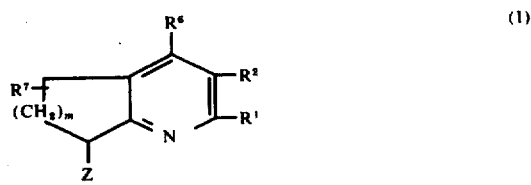

(1)

or a pharmaceutically acceptable acid addition salt thereof, wherein

Z is —CONH₂, —CSNH₂ or —CN;

$R^1$, $R^2$ and $R^6$ are independently hydrogen, trifluoromethyl, alkyl of 1 to 6 carbon atoms, phenylalkyl of 7 to 12 carbon atoms or phenyl, or R¹ and R² taken together represent an R⁷ substituted alkylene chain, substituted alkylene chain consisting of 3 to 5 carbon atoms, inclusive;

R⁷ is hydrogen, alkyl of 1 to 6 carbon atoms, gem-di-n-alkyl in which each alkyl group has 1 to 6 carbon atoms, phenylalkyl of 7 to 12 carbon atoms or phenyl;

$m$ is one of the integers 1, 2 or 3;

with the proviso that when R¹ and R² or R² and R⁶ are both alkyl, they are normal or secondary alkyl;

which process comprises the steps of treating a compound of formula II

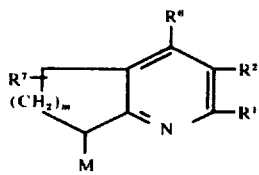

wherein
R¹, R², R⁶, R⁷ and $m$ are defined above and M is sodium, potassium, lithium, MgCl, MgBr or MgI;
with a compound of the formula:

wherein
each R group is independently alkyl of 1 to 6 carbon atoms, phenyl or aralkyl of 7–12 carbon atoms;
Y is oxygen or sulfur; and
X is an integer from 0 to 3, inclusive
followed by hydrolysis or alcoholysis of the product, with the proviso that when Z is —CN the molar ratio of $R_xSi(NCY)_{4-x}$ to compound II is at least 2:1, X is 3 and Y is sulfur, and with the additional proviso that when Z is —CONH₂ or —CSNH₂, the molar ratio of $R_xSi(NCY)_{4-x}$ to compound II is less than 4:1.

2. A process as claimed in claim 1, wherein the starting material of formula II is prepared in situ by treatment of a compound of formula II in which M is hydrogen with a metal amide of the formula MA wherein M is sodium, potassium or lithium and A is an amido group of a secondary camine selected from the group consisting of diethylamine, di-isopropylamine, di-tertiarybutyl amine, di-n-decylamine, dicyclohexylamine, N-tertiaryamyl-N-t-butylamine, N-isopropyl-N-cyclohexylamine, N(1'-ethylcyclohexyl)-1,1,3,3,-tetramethylbutylamine, piperidine and 2,2,6,6-tetramethylpiperidine.

3. A process as claimed in claim 2, where A is di-isopropylamine.

4. A process as claimed in claim 1 wherein M is lithium.

5. A process as claimed in claim 1 wherein $m$ is 2.

6. A process as claimed in claim 1 wherein the starting material of formula II is 5,6,7,8-tetrahydroquinoline or a substituted 5,6,7,8-tetrahydroquinoline in which at least one of groups R¹, R², R⁶ or R⁷ is alkyl of 1 to 6 carbon atoms, with the proviso that adjacent alkyl groups are normal or secondary.

7. A process as claimed in claim 6 wherein the starting material of formula II is one in which R¹, R² and R⁶ are independently selected from hydrogen and methyl and R⁷ is hydrogen.

8. A process as claimed in claim 7 wherein the starting material of formula II is a 3- or 4-methyl-5,6,7,8-tetrahydroquinoline.

9. A process of claim 1 where the reactant $R_xSi(NCY)_{4-x}$ is a trialkylsilyl isothiocyanate in which each alkyl group has from 1 to 6 carbon atoms.

10. A process of claim 9 wherein the reactant $R_xSi(NCY)_{4-x}$ is trimethylsilyl isothiocyanate.

* * * * *

UNITED STATES PATENT OFFICE
CERTIFICATE OF CORRECTION

PATENT NO. : 4,000,142
DATED : December 28, 1976
INVENTOR(S) : Adrian Charles Ward Curran & Robin Gerald Shepherd It is certified that error appears in the above-identified patent and that said Letters Patent are hereby corrected as shown below:

Col. 11, line 3 - "substituted" should read "said".
Col. 11, line 2 - "substituted" is incorrectly spelt.
Col. 12, line 8 - "camine" should read "amine".
Col. 3, line 31 - "ethyl" should read "methyl".
Col. 3, line 50 - "compound" is incorrectly spelt.
Col. 4, line 34 - "solution" is incorrectly spelt.
col. 4, line 44 - "triturated" is incorrectly spelt.
Col. 4, line 57 - 7.3 in the first parenthesis should read "7.3 g.".
Col. 4, line 68 - "with" is incorrectly spelt.
Col. 6, line 44 - "amounts" is incorrectly spelt.
Col. 10, line 1 - In the parenthesis 5.65 ag should read 5.65 g.

Signed and Sealed this

Fourth Day of October 1977

[SEAL]

Attest:

RUTH C. MASON
Attesting Officer

LUTRELLE F. PARKER
Acting Commissioner of Patents and Trademarks